(12) United States Patent
Vail et al.

(10) Patent No.: US 8,915,923 B2
(45) Date of Patent: Dec. 23, 2014

(54) PATELLA RESECTION ASSEMBLY

(75) Inventors: Thomas P. Vail, San Francisco, CA (US); Abraham P. Wright, Winona Lake, IN (US)

(73) Assignee: Depuy (Ireland), Cork (IE)

( * ) Notice: Subject to any disclaimer, the term of this patent is extended or adjusted under 35 U.S.C. 154(b) by 256 days.

(21) Appl. No.: 13/548,628

(22) Filed: Jul. 13, 2012

(65) Prior Publication Data

US 2013/0079784 A1 Mar. 28, 2013

Related U.S. Application Data

(60) Provisional application No. 61/540,058, filed on Sep. 28, 2011.

(51) Int. Cl.
*A61B 17/58* (2006.01)
*A61B 17/60* (2006.01)
*A61F 2/00* (2006.01)
*A61B 17/15* (2006.01)
*A61B 17/00* (2006.01)

(52) U.S. Cl.
CPC ..... *A61B 17/158* (2013.01); *A61B 2017/00464* (2013.01)
USPC .............................. 606/88; 606/130; 606/87

(58) Field of Classification Search
CPC .................................................... A61B 17/158
USPC ............................................. 606/130, 87, 88
See application file for complete search history.

(56) References Cited

U.S. PATENT DOCUMENTS

| 2,181,746 A | 11/1939 | Siebrandt |
| 3,835,849 A | 9/1974 | McGuire |
| D260,927 S | 9/1981 | Glenn |
| D281,622 S | 12/1985 | Diamond |
| 4,565,192 A | 1/1986 | Shapiro |
| 4,633,862 A | 1/1987 | Petersen |
| 5,002,547 A | 3/1991 | Poggie et al. |
| 5,021,055 A | 6/1991 | Burkinshaw |
| 5,108,401 A | 4/1992 | Insall et al. |
| 5,116,338 A | 5/1992 | Poggie |
| 5,129,907 A | 7/1992 | Heldreth |

(Continued)

FOREIGN PATENT DOCUMENTS

| EP | 992222 A3 | 4/2000 |
| EP | 2574314 A1 | 4/2013 |
| WO | 9945856 A1 | 9/1999 |
| WO | 2008112996 A1 | 9/2008 |

OTHER PUBLICATIONS

Depuy International Ltd., PFC Sigma Rotating Platform Knee System with MBT Tray, Surgical Technique Brochure, 2003, (43 pages), Cat. No. 9068-96-000, DePuy International Ltd., Leeds, England.

(Continued)

*Primary Examiner* — David Bates
*Assistant Examiner* — Samuel Hanna

(57) ABSTRACT

A patella resection assembly comprises a modular handle and claw member. The claw member is reversibly mountable on the handle so that the same modules may be used to resect the patellae of both the right and the left knees. The handle has an adjustable member that carries a bone-gripping member. Linear movement of the adjustable member allows the same patella resection assembly to be used to securely grip patellae of various sizes.

2 Claims, 3 Drawing Sheets

(56) References Cited

U.S. PATENT DOCUMENTS

| | | |
|---|---|---|
| 5,129,908 A | 7/1992 | Petersen |
| 5,147,365 A | 9/1992 | Whitlock et al. |
| 5,222,955 A | 6/1993 | Mikhail |
| 5,250,050 A | 10/1993 | Poggie et al. |
| 5,284,482 A | 2/1994 | Mikhail |
| 5,284,485 A | 2/1994 | Kammerer et al. |
| 5,382,254 A | 1/1995 | McGarry et al. |
| 5,415,663 A | 5/1995 | Luckman et al. |
| 5,470,328 A | 11/1995 | Furnish et al. |
| 5,484,451 A | 1/1996 | Akopov et al. |
| D367,531 S | 2/1996 | Price et al. |
| 5,520,692 A | 5/1996 | Ferrante |
| 5,536,271 A | 7/1996 | Daly |
| 5,542,947 A | 8/1996 | Treacy |
| D373,635 S | 9/1996 | Price et al. |
| 5,575,793 A | 11/1996 | Carls et al. |
| 5,582,615 A | 12/1996 | Foshee et al. |
| 5,593,450 A | 1/1997 | Scott et al. |
| 5,611,802 A | 3/1997 | Samuelson et al. |
| 5,626,607 A | 5/1997 | Malecki et al. |
| 5,667,512 A | 9/1997 | Johnson |
| 5,716,362 A | 2/1998 | Treacy |
| 5,827,279 A | 10/1998 | Hughett et al. |
| 5,941,884 A | 8/1999 | Corvelli et al. |
| 5,944,723 A | 8/1999 | Colleran |
| 5,968,051 A | 10/1999 | Luckman et al. |
| 6,010,509 A | 1/2000 | Delgado et al. |
| 6,056,754 A | 5/2000 | Haines et al. |
| 6,074,425 A | 6/2000 | Pappas |
| 6,190,391 B1 | 2/2001 | Stubbs |
| 6,205,884 B1 | 3/2001 | Foley et al. |
| D459,474 S | 6/2002 | Bratt et al. |
| 6,419,675 B1 | 7/2002 | Gallo, Sr. |
| D463,550 S | 9/2002 | Sherman |
| 6,551,316 B1 | 4/2003 | Rinner |
| 6,855,150 B1 | 2/2005 | Linehan |
| 6,866,667 B2 | 3/2005 | Wood et al. |
| D549,331 S | 8/2007 | Tomatsu et al. |
| 7,344,540 B2 | 3/2008 | Smucker et al. |
| 7,566,335 B1 * | 7/2009 | Scott et al. ............... 606/88 |
| 7,632,279 B2 | 12/2009 | Bastian |
| 7,780,594 B2 | 8/2010 | Hutton |
| 7,806,899 B2 | 10/2010 | Hogg et al. |
| 7,878,989 B2 | 2/2011 | McMinn |
| 7,891,071 B2 | 2/2011 | Collazo |
| D634,011 S | 3/2011 | Phillips et al. |
| D638,541 S | 5/2011 | Claypool |
| 7,972,383 B2 | 7/2011 | Goldstein et al. |
| D642,678 S | 8/2011 | Dockstader et al. |
| D646,389 S | 10/2011 | Claypool et al. |
| 8,216,242 B2 | 7/2012 | Marchyn |
| 2002/0049377 A1 * | 4/2002 | Moctezuma De La Barrera et al. ............... 600/407 |
| 2002/0115987 A1 | 8/2002 | Hildwein et al. |
| 2004/0153066 A1 | 8/2004 | Coon |
| 2004/0162561 A1 | 8/2004 | Marchyn et al. |
| 2005/0240196 A1 | 10/2005 | Davis et al. |
| 2006/0142777 A1 | 6/2006 | Bastian |
| 2007/0118141 A1 | 5/2007 | Marchyn et al. |
| 2007/0162031 A1 | 7/2007 | Hogg |
| 2007/0233142 A1 | 10/2007 | Oliver |
| 2007/0260227 A1 | 11/2007 | Phan |
| 2008/0097450 A1 | 4/2008 | Brown et al. |
| 2008/0114366 A1 | 5/2008 | Smucker et al. |
| 2008/0177394 A1 | 7/2008 | Chauhan |
| 2008/0228190 A1 | 9/2008 | Sherry et al. |
| 2008/0306484 A1 | 12/2008 | Coon |
| 2009/0088753 A1 * | 4/2009 | Aram et al. ............... 606/79 |
| 2009/0264737 A1 | 10/2009 | Haechler et al. |
| 2009/0326661 A1 | 12/2009 | Wright et al. |
| 2010/0030223 A1 | 2/2010 | Kellar |
| 2010/0152742 A1 | 6/2010 | Nevelös et al. |
| 2010/0168753 A1 | 7/2010 | Edwards et al. |
| 2011/0066193 A1 | 3/2011 | Lang |
| 2012/0078261 A1 | 3/2012 | Kecman et al. |
| 2013/0023883 A1 | 1/2013 | Wright |
| 2013/0023890 A1 | 1/2013 | Kecman |
| 2013/0030443 A1 | 1/2013 | Wright |
| 2013/0030539 A1 | 1/2013 | Wright |
| 2013/0035693 A1 | 2/2013 | Wright |
| 2013/0079788 A1 | 3/2013 | Spencer Jones |
| 2013/0079789 A1 | 3/2013 | Randle |
| 2013/0211410 A1 | 8/2013 | Landes |

OTHER PUBLICATIONS

Depuy Orthopaedics, Inc., LCS High Performance Instruments, Surgical Technique Guide, 2008, (44 pages), Pub. No. 0612-85-506, DePuy Orthopaedics, Inc., Warsaw, IN.

Depuy Orthopaedics, Inc., Sigma High Performance Instruments, Classic Surgical Technique, 2010, (52 pages), Pub. No. 0612-89-510, DePuy Orthopaedics, Inc., Warsaw, IN.

Depuy Orthopaedics, Inc., Sigma High Performance Instruments, Design Rationale, 2009, (12 pages), Pub. No. 0612-54-506 (Rev.2), DePuy Orthopaedics, Inc., Warsaw, IN.

European Search Report, European Patent Application No. 11175824.9-2310, Dec. 16, 2011, (8 pages).

European Search Report, European Patent Application No. 11175824.9-2310, Mar. 1, 2013 (7 pages).

* cited by examiner

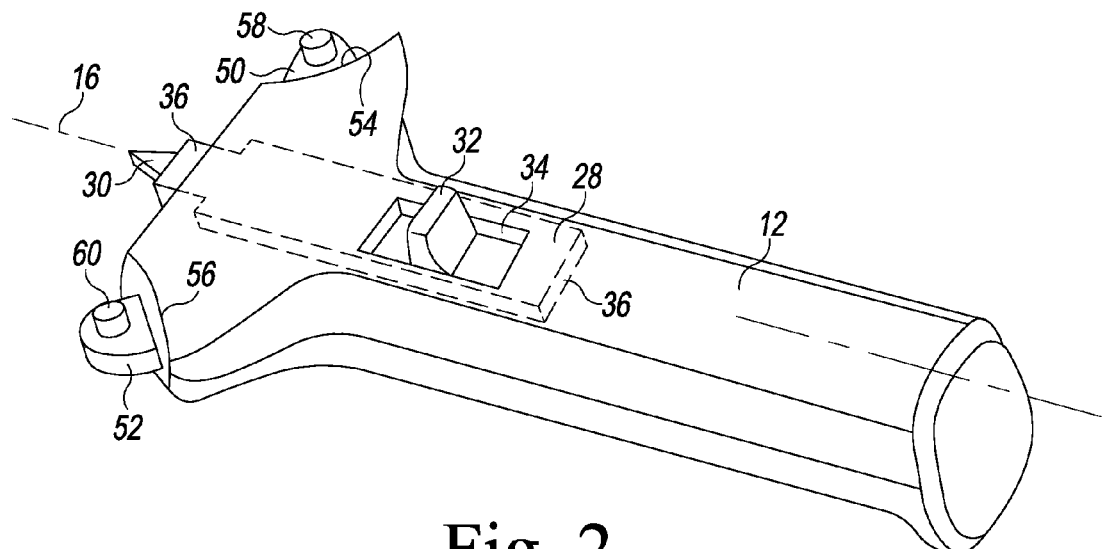
Fig. 2
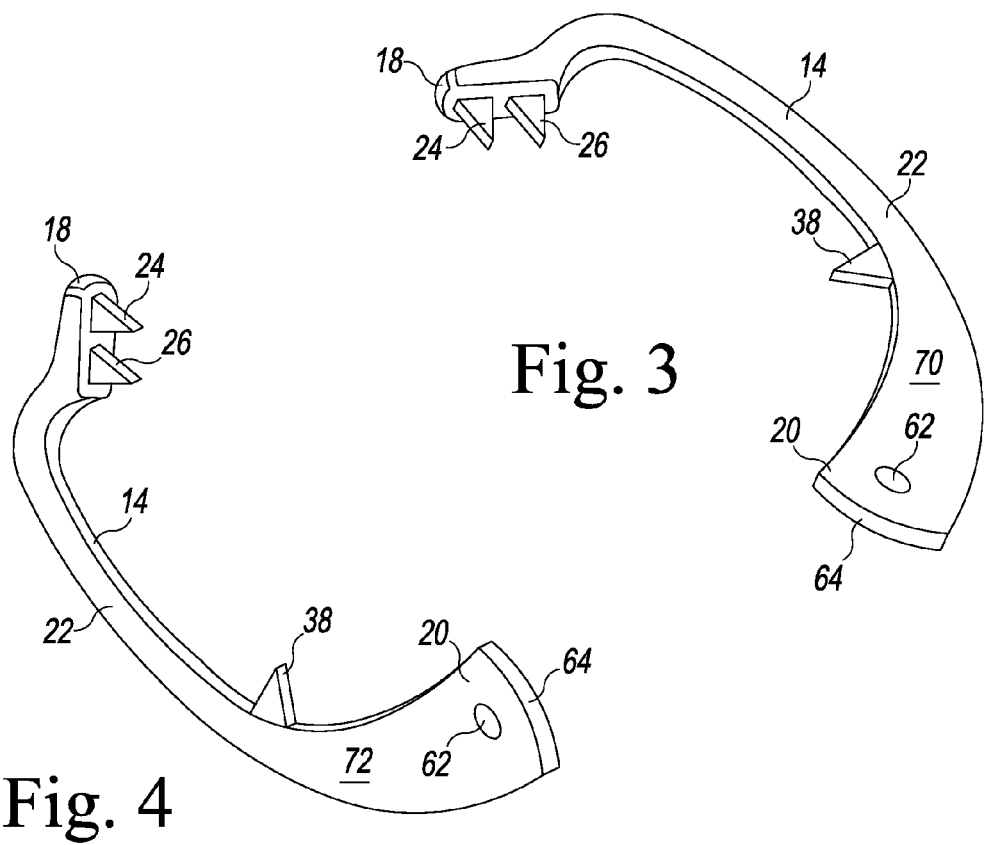
Fig. 3
Fig. 4

PATELLA RESECTION ASSEMBLY

CROSS-REFERENCE TO RELATED APPLICATION

This application claims priority to U.S. Prov. App. No. 61/540,058 filed Sep. 28, 2011, entitled "Patella Resection Assembly," which is incorporated by reference herein in its entirety.

TECHNICAL FIELD

The present disclosure relates generally to orthopaedic surgical instruments and more particularly to patella resectioning guides.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella. To prepare the patella, an orthopaedic surgeon first resects the posterior dome side of the patient's natural patella to secure the prosthetic component thereto. In use, the patella component articulates with the patient's natural or prosthetic femur during extension and flexion of the patient's knee.

To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

In resecting the patella, surgeons frequently perform the resection free-hand. However, free-hand cutting the patella is not as accurate as a guided resection. Moreover, it is important that a sufficient amount of bone stock remain after resection to accept the fixation means for the patellar prosthesis and to maintain the integrity of the remaining patella. To ensure that the patella implant is properly positioned and that an appropriate amount of bone remains after resection, a resection guide is needed.

Depending on a number of factors, including the size of the patient, native patellae are of substantially different sizes. Accordingly, if a resection guide is to be used, either the guide must be provided in a plurality of sizes to accommodate variations in patellae size or an adjustable resection guide must be used.

SUMMARY

The present invention provides an adjustable patella resection guide that assists the surgeon in performing a resection while the patella is gripped securely.

In an illustrative embodiment, the present invention provides a patella resection assembly comprising a handle and a discrete claw member. The handle has a longitudinal axis. The claw member extends from the handle to a first free end aligned along a longitudinal plane through the longitudinal axis of the handle. The claw member has a second end mounted to the handle and a flat surface for guiding a saw blade. A first gripping member is at the first free end of the claw member and extends toward the handle. An adjustable member is movably mounted on the handle, and is selectively movable in a linear direction along the longitudinal axis of the handle toward and away from the first free end of the claw member. A second gripping member is on the adjustable member and extends toward the first free end of the claw member. The first free end of the claw member is spaced from the handle. The claw member and the handle define an opening between the first free end of the claw member and the adjustable member. Linear movement of the adjustable member changes the dimension of the opening between the first free end of the claw member and the adjustable member along the longitudinal axis. The claw member and the handle have complementary mounting members for removably mounting the claw member on the handle in a first orientation and a second orientation. In the first orientation a majority of the claw member is located on one side of the longitudinal plane and the position of the first gripping member is fixed with respect to the handle. In the second orientation a majority of the claw member is located on the other side of the longitudinal plane and the position of the first gripping member is fixed with respect to the handle.

In a more particular embodiment, the patella resection assembly further comprises a third gripping member extending from the claw member toward the opening at a position spaced from the free end of the claw member.

In a more particular embodiment, the handle includes a pair of spaced mounting flanges and an edge adjacent to each flange, and the second end of the claw member includes an edge. In this embodiment, the edges of the handle adjacent to the mounting flanges and the second end of the claw member have complementary shapes.

BRIEF DESCRIPTION OF THE DRAWINGS

The detailed description particularly refers to the following figures, in which:

FIG. 2 is a perspective view of the modular handle portion of the patella resection assembly of FIG. 1;

FIG. 3 is a perspective view of the modular claw member of the patella resection assembly of FIG. 1 in a first orientation, showing the top surface of the claw member;

FIG. 4 is a perspective view of the modular claw member of FIG. 3 in a second orientation, showing the bottom surface of the claw member;

DETAILED DESCRIPTION OF THE DRAWINGS

Figure 1:
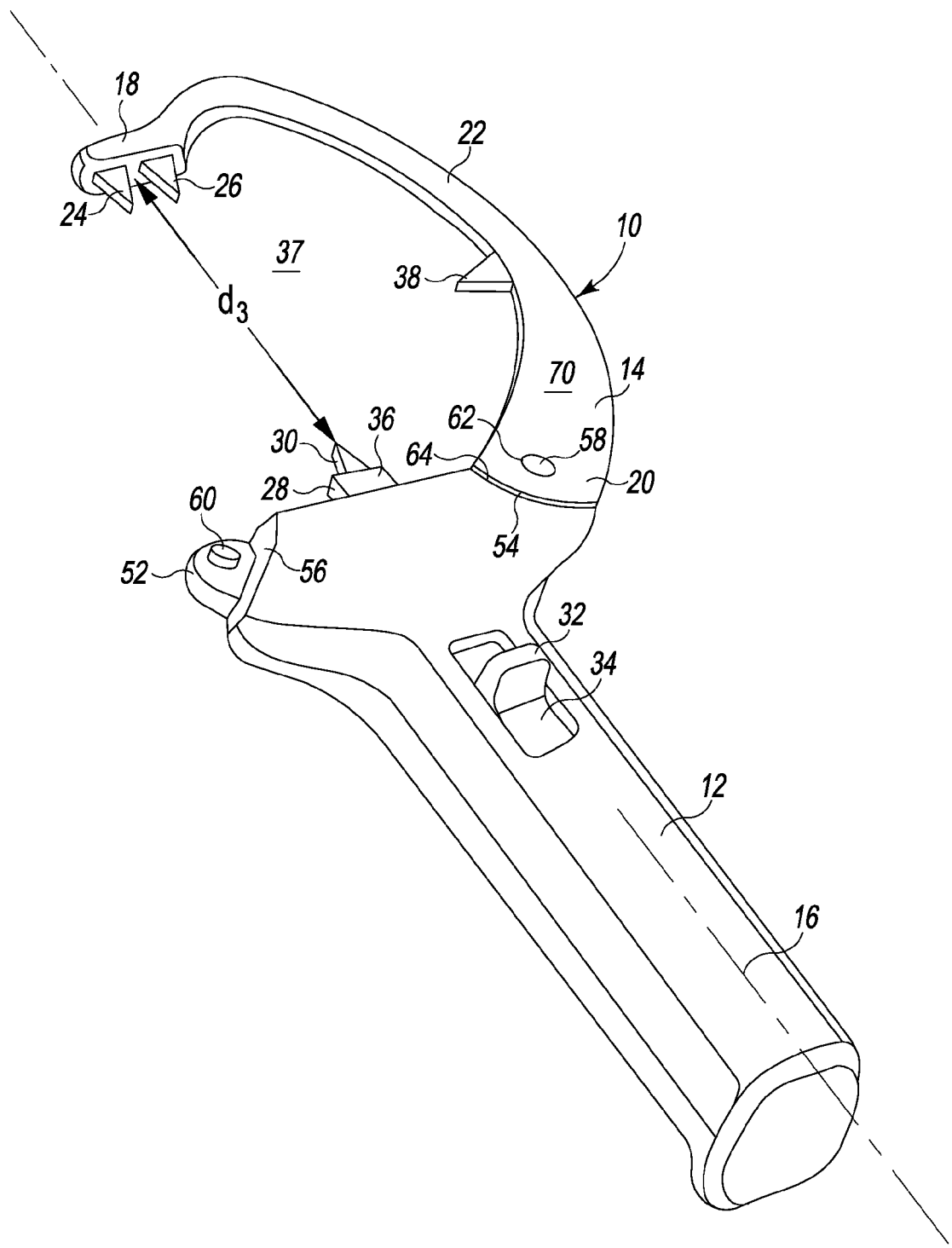
FIG. 1 is a perspective view of one embodiment of a patella resection assembly incorporating the principles of the present invention showing the modular claw member in a first orientation and an adjustable member in an intermediate position.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, a first embodiment of a patella resection assembly 10 is illustrated. The illustrated patella resection assembly 10 comprises a handle 12 and a discrete claw member 14. The handle 12 has a central longitudinal axis 16. The claw member 14 extends outwardly from the handle 12 to a free end 18 aligned along a longitudinal plane through the longitudinal axis 16 of the handle. The claw member 14 also has a second end 20 mounted to the handle 12, a flat surface 22 for guiding a saw blade (not shown) during resection of the patella and a first bone-gripping member 24 at the first free end 18. The illustrated first bone-gripping member 24 comprises a sharp tooth extending toward the handle 12. In the embodiment of FIGS. 1 and 3-7, the free end 18 of the claw member 14 also includes a second sharp tooth 26.

The patella resection assembly 10 of FIG. 1 also includes an adjustable member 28 mounted on the handle 12. The adjustable member 28 is selectively movable in a linear direction along the longitudinal axis 16 of the handle 12 toward and away from the first free end 18 of the claw member 14. The adjustable member 28 has a free end that includes a second bone-gripping member 30; in the illustrated embodiment, the second bone-gripping member 30 comprises a sharp tooth extending toward the first free end 18 of the claw member 14.

Figure 5:
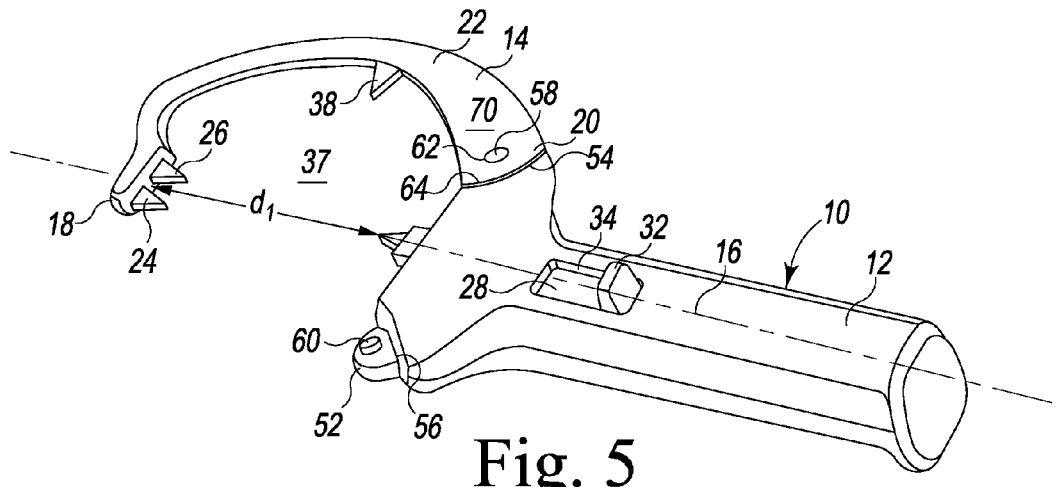
FIG. 5 is a perspective view of the patella resection assembly of FIG. 1, shown with the adjustable member is a fully retracted position.
Figure 6:
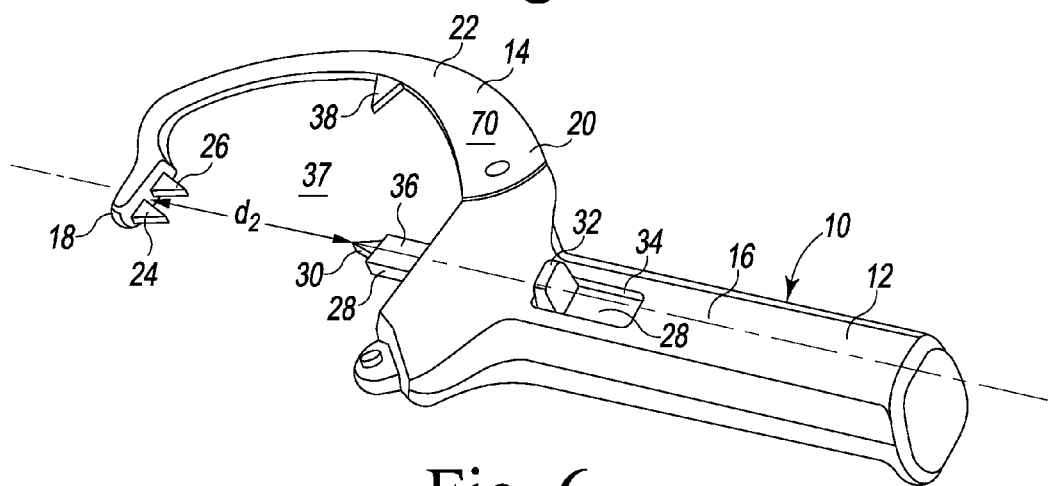
FIG. 6 is a perspective view of the patella resection assembly of FIG. 1, shown with the adjustable member is a fully extended position.
Figure 7:
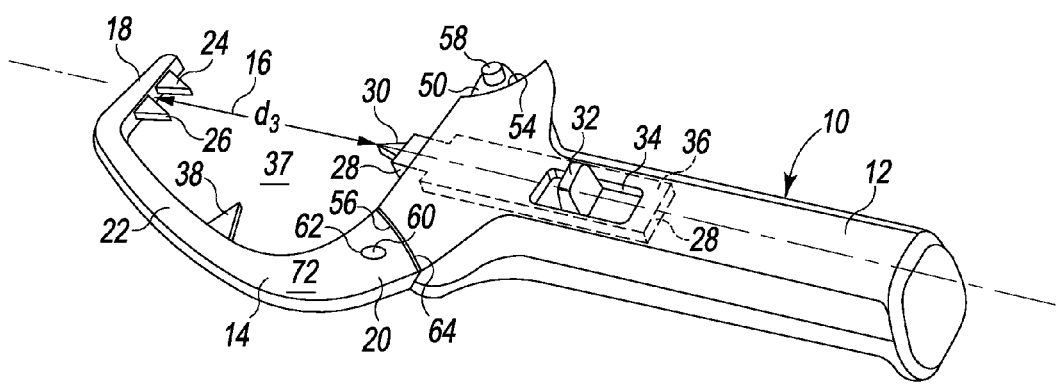
FIG. 7 is a perspective of the patella resection assembly of FIG. 1, shown with the claw member is a second orientation and the adjustable member in an intermediate position.

As shown in FIGS. 1, 2 and 5-7, the adjustable member 28 includes an upstanding tab 32 moveable within an open slot 34 formed in the body of the handle 12. As shown in FIGS. 2 and 7, in the first illustrated embodiment, the tab 32 of the adjustable member 28 is connected to or integral with an elongate body 36 received and longitudinally slidable within a slot or compartment formed within the handle 12. The elongate body 36 extends out of an opening (not shown) at one end of the handle 12 to an end. The second bone-gripping member or tooth 30 is disposed at this end of the elongate body 36.

As shown in FIGS. 1 and 5-7, the first free end 18 of the claw member 14 is spaced from the handle 12. The claw member 14 and the handle 12 define an opening 37 between the first free end 18 of the claw member 14 and the adjustable member 28 on the handle 12. The opening 37 is sized and shaped to receive a patient's patella, and more particularly, to receive a variety of sizes of patellae. The first bone-gripping member 24 and second tooth 26 extend into the opening 37 toward the handle 12. The second bone-gripping member 30 on the adjustable member 28 extends toward the first free end 18 of the claw member 14. The first bone-gripping member 24, tooth 26 and second bone-gripping member 30 are provided for gripping the periphery of the patient's patella to stabilize the position of the patella during resection. As described in more detail below, the longitudinal position of the second bone-gripping member 30 is variable so that the patella resection assembly 10 can be used to grip the peripheries of a variety of sizes of patellae. To provide additional stability, a third bone-gripping member may be provided at a third position, spaced from the positions of the first and second bone-gripping members 24, 30; an example of such a third bone-gripping member is shown at 38 in FIGS. 1 and 3-7, extending toward the opening 37 from a position along the side of the claw member 14.

The variable position of the second bone-gripping member 30 is illustrated in FIGS. 1 and 5-6. As shown in FIG. 5, by sliding the tab 32 away from the free end 18 of the claw member 14 to one end of the open slot 34, the second bone-gripping member or tooth 30 can be fully retracted into the interior of the handle 12. With the adjustable member 28 in the fully retracted position, the opening 37 defined by the first free end 18 of the claw member 14 and the adjustable member 28 is maximized at the dimension $d_1$ as shown in FIG. 5. By sliding the tab 32 toward the free end 18 of the claw member 14 and to the opposite end of the open slot 34, the adjustable member 28 can be fully extended. With the adjustable member 28 in the fully extended position, the opening 37 defined by the first free end 18 of the claw member 14 and the adjustable member 28 is minimized at the dimension $d_2$ as shown in FIG. 6. The adjustable member 28 may also be set at any position between the two extremes shown in FIGS. 5 and 6, such as at the intermediate position shown in FIGS. 1 and 7. With the adjustable member 28 in an intermediate position, the opening 37 defined by the first free end 18 of the claw member 18 and the adjustable member 28 is an intermediate dimension $d_3$ as shown in FIG. 1. In all of these positions, the position of the claw member 14 remains fixed with respect to the handle 12.

Although not illustrated, it should be understood that the handle 12 and adjustable member 28 may include a variety of structures to lock the adjustable member 28 in preselected positions. For example, a releasable linear ratchet and pawl or the like could be employed. Alternatively or additionally, the handle 12 and adjustable member 28 may include a variety of structures to bias the adjustable member 28 toward a particular position. For example, a spring could be held in a recess in the handle and bear against some portion of the adjustable member to bias the adjustable member toward the fully retracted position shown in FIG. 5 or the fully extended position shown in FIG. 6.

The illustrated embodiment of the patella resection assembly 10 is modular. The handle 12 and claw member 14 are discrete components that are easily assembled and disassembled. FIG. 2 illustrates the modular handle 12. FIGS. 3 and 4 illustrate the modular claw member 14. The handle 12 and claw member 14 have complementary mounting members described in more detail below for removably mounting the claw member 14 on the handle 12 in first and second orientations. As described in more detail below, in the illustrated embodiment, the complementary mounting members comprise pegs and holes, although it should be understood that other complementary mounting members could be used.

As shown in FIG. 2, the illustrated handle 12 includes a pair of spaced mounting flanges 50, 52 adjacent to curved edges 54, 56. Mounting pegs 58, 60 extend upward from the flanges 50, 52. The handle 12 is substantially symmetrical about a plane through the longitudinal axis 16, so that the flanges 50, 52, curved edges 54, 56 and pegs 58, 60 are mirror images of each other.

As shown in FIGS. 3 and 4, the illustrated discrete claw member 14 includes a through hole 62 near the second end 20 that is sized and shaped to receive one of the pegs 58, 60. The second end 20 of the illustrated discrete claw member 14 also has a curved edge 64 that is complementary in shape to the curved edges 54, 56 of the handle 12. Thus, the claw member 14 may be selectively mounted on both sides of the handle 12 so that the claw member 14 may be selectively oriented in a first orientation as shown in FIGS. 1, 5 and 6 and a second orientation as shown in FIG. 7. In the first orientation, a majority of the claw member 14 located on one side of the longitudinal plane through the longitudinal axis 16 of the handle, and the interaction of the peg 58 and hole 62 and complementary edges 54, 64 fix the position of the claw member 14 with respect to the handle 12 so that the position of the first gripping member 24 is fixed with respect to the handle 12. In the second orientation, a majority of the claw member 14 located on the other side of the longitudinal plane through the longitudinal axis 16 of the handle, and the interaction of the peg 60 and hole 62 and complementary edges 56, 64 fix the position of the claw member 14 with respect to the handle 12 so that the position of the first gripping member 24 is fixed with respect to the handle 12.

It should be understood that the pegs 58, 60 and hole 62 may be reversed, so that holes are provided in the flanges 50, 52 and a peg extending out from both sides of the second end 20 of the claw member 14. It should also be understood that the complementary mounting features described above of the handle 12 and claw member 14 are illustrative only. Other structures for mounting the claw member 14 on the handle 12 may be used, and locking features to temporarily hold the claw member 14 on the handle 12 may be included.

It should be understood that the complementary mounting features of the handle 12 and claw member 14 described above are illustrative only. Other structures for mounting the claw member 14 on the handle 12 may be used, and releasable locking features may also be included.

The illustrated claw member 14 has a top surface 70 and a bottom surface 72. These surfaces 70, 72 are planar and flat; when resecting the patella, the surgeon may guide the saw blade to make a planar cut by resting the flat portion of the saw blade against one of these surfaces 70, 72 of the claw member 14. Either the top surface 70 or the bottom surface 72 may be used for guiding the saw blade; accordingly, the claw member 14 can be mounted on either side of the longitudinal plane through the longitudinal axis 16.

It should be understood that additional features may be included to define one or more guide slots along the surfaces 70, 72 of the claw member 14 if desired.

To use the patella resection assembly 10 of the present invention, the surgeon would make a standard incision and then partially or fully evert the patient's patella to expose the posterior side of the patella. If not pre-assembled, the surgeon would assemble the claw member 14 and the handle 12 by inserting the peg 58 or 60 through the hole 62 in the claw member 14. With the adjustable member 28 retracted, the claw member 14 portion of the assembly may be introduced to the surgical site and moved across the patella, in, for example, a superior to inferior direction until the edge (such as the superior edge) of the patella contacts one of the gripping members (such as gripping member 38). The opening 37 between the free end 18 of the claw member 14 and the adjustable member 28 on the handle 12 allows the patella to be received between the bone-gripping members 24, 30. The adjustable member 28 may then be extended until opposite portions of the edge of the patella are held between the opposing bone-gripping members 24, 30. Thus, the patella may be clamped through three-point contact and the patella may be resected while it is gripped securely.

It will be appreciated that the design of the illustrated patella resection assembly 10 allows for its use in minimally invasive surgical techniques. Since the resection guide assembly only contacts a portion of the patella, it may be introduced in a superior-inferior direction rather than in a posterior-anterior direction, thus allowing for a less invasive approach.

It will also be appreciated that the modular design of the illustrated patella resection assembly 10 allows for the same instrument to be used for both the right and the left knees, with similar approaches for each. Thus, inventory may be reduced.

Another advantage of the modular design of the illustrated patella resection assembly 10 is that the modular design allows for selection of the most appropriate and economical material to be used to make the constituent elements. For example, the handle 12 could be made of metal, plastic or other material. For example, the handle 12 and adjustable member 28 may be made relatively inexpensively by injection molding of suitable polymers. The claw member 14 could also be made of metal, plastic or other material, although it may be preferred to construct the claw member such that at least surfaces 70 and 72 are metal so that appropriate support is provided for the saw blade. In addition, processes such as those described in U.S. Patent Publication No. 2010168753A1, entitled "Orthopaedic Cutting Block Having a Chemically Etched Metal Insert and Method of Manufacturing," the complete disclosure of which is incorporated by reference herein, may be used to make a combination polymer-metal claw member 14.

Additional features may be added to the illustrated patella resection assembly 10. For example, a stylus assembly could be provided for mounting across the opening 37 for setting the appropriate resection level. Such a stylus could be removably supported by the free end 18 of the claw member 14 and a portion of the handle 12, for example.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

We claim:
1. A patella resection assembly comprising:
a handle having a longitudinal axis;
a claw member extending from the handle to a first free end aligned along a longitudinal plane through the longitudinal axis of the handle, the claw member having a second end mounted to the handle and a flat surface for guiding a saw blade;
a first gripping member at the first free end of the claw member and extending from the first free end of the claw member toward the handle when the claw member is assembled on the handle; and
an adjustable member movably mounted on the handle, the adjustable member being selectively movable in a linear direction along the longitudinal axis of the handle toward and away from the first free end of the claw member;

a second gripping member on the adjustable member and extending from the adjustable member toward the first free end of the claw member;

wherein:

the first free end of the claw member is spaced from the handle;

the claw member and the handle define an opening between the first free end of the claw member and the adjustable member;

linear movement of the adjustable member relative to the handle changes the dimension of the opening between the first free end of the claw member and the adjustable member along the longitudinal axis;

the claw member and the handle have complementary mounting members for removably mounting the claw member on the handle in a first orientation and a second orientation;

the complementary mounting members are independent of the adjustable member so that when the claw member is assembled with the handle the position of the first gripping member is independent of linear movement of the adjustable member;

in the first orientation a majority of the claw member is located on one side of the longitudinal plane and the position of the first gripping member is fixed with respect to the handle;

in the second orientation a majority of the claw member is located on the other side of the longitudinal plane and the position of the first gripping member is fixed with respect to the handle;

the complementary mounting member of the handle includes a pair of spaced mounting flanges and an edge adjacent to each mounting flange;

the complementary mounting member on the second end of the claw member includes an edge; and the edges of the handle adjacent to the mounting flanges and the second end of the claw member have complementary shapes so that in the first orientation the complementary edges of the claw member and one mounting flange prevent rotation of the claw member with respect to the longitudinal plane and in the second orientation the complementary edges of the claw member and the other mounting flange prevent rotation of the claw member with respect to the longitudinal plane.

2. The patella resection assembly of claim 1 further comprising a third gripping member extending from the claw member toward the opening at a position spaced from the free end of the claw member.

* * * * *